United States Patent [19]

Ruffing et al.

[11] Patent Number: 4,913,728
[45] Date of Patent: Apr. 3, 1990

[54] SUBSTITUTED-4-ALKYLTHIOALKANE-SULFONANILIDES AND OPERATIVES

[75] Inventors: Sharon L. Ruffing, Oakdale; James R. Throckmorton, Woodbury, both of Minn.

[73] Assignee: Minnesota Mining and Manufacturing Company, St. Paul, Minn.

[21] Appl. No.: 553,874

[22] Filed: Nov. 21, 1983

Related U.S. Application Data

[63] Continuation of Ser. No. 223,112, Jan. 7, 1981, abandoned, which is a continuation-in-part of Ser. No. 7,036, Jan. 29, 1979, abandoned.

[51] Int. Cl.$^4$ ............................................. A01N 41/06
[52] U.S. Cl. .......................................... 71/103; 71/78; 564/97; 564/99
[58] Field of Search ...................... 71/98, 103; 564/97, 564/99

[56] References Cited

U.S. PATENT DOCUMENTS

| | | | |
|---|---|---|---|
| 3,639,474 | 2/1972 | Harrington et al. | 71/103 |
| 3,734,710 | 5/1973 | Lukaszczyk et al. | 71/103 |
| 3,840,597 | 10/1974 | Moore et al. | 71/103 |
| 3,856,856 | 12/1974 | Moore et al. | 71/103 |
| 3,856,859 | 12/1974 | Moore et al. | 564/97 |
| 3,981,914 | 9/1976 | Mursch et al. | 71/103 |
| 3,996,277 | 12/1976 | Fridinger et al. | 71/103 |
| 4,341,901 | 7/1982 | Ruffing et al. | 564/99 |

FOREIGN PATENT DOCUMENTS

| | | | |
|---|---|---|---|
| 865843 | 10/1978 | Belgium | 71/103 |
| 2703477 | 8/1978 | Fed. Rep. of Germany | 71/103 |

*Primary Examiner*—Catherine L. Mills
*Attorney, Agent, or Firm*—Donald M. Sell; Walter N. Kirn; Philip M. Goldman

[57] ABSTRACT

Alkane- and monohaloalkane-sulfonanilides substituted in the para position by alkylthio, alkylsulfinyl and alkylsulfonyl groups and additionally substituted by halogen and optionally by trifluoromethyl and agriculturally acceptable salts thereof are useful herbicides.

4 Claims, No Drawings

SUBSTITUTED-4-ALKYLTHIOALKANE-SULFONANILIDES AND OPERATIVES

This is a continuation of application Ser. No. 223,112 filed January 7, 1981, abandoned, which is a continuation-in-part of application Ser. No. 7,036 filed January 29, 1979, now abandoned.

BACKGROUND OF THE INVENTION

This invention relates to halo-substituted methane- and chloromethane-sulfonanilides substituted in the para position by alkylthio, alkylsulfinyl or alkylsulfonyl groups and optionally substituted by trifluoromethyl and to agriculturally acceptable salts thereof. The compounds of the invention are active plant growth modifying agents. The invention also relates to plant growth modifying compositions comprising the compounds of the invention dispersed in agriculturally acceptable extending media and to the use of the compounds to modify the growth of higher plants. Methods for preparing the compounds and intermediates in their preparation are also included.

Plant growth modification as defined herein consists of all deviations from natural development, for example, defoliation, stimulation, stunting, inhibition, desiccation, tillering, and even death. This plant growth modifying activity is generally observed as the compounds of the invention begin to interfere with certain processes within the plant. If vital processes are affected, the plant will die if treated with a sufficient dose of the compound and the compound can be termed a herbicide relative to that plant. If the plant is a weed, the compound can be used to control or kill it and this is particularly valuable when a compound controls or kills a weed at an application rate that has little or no effect on a crop plant. I.e., it can serve as a selective herbicide to control or kill the weed in the presence of that crop. On the other hand, the growth of desirable plants can sometimes be modified beneficially, e.g., to suppress undesirable growth or to improve the quantity or quality of the harvest from the plant or to serve as a harvest aid. Such beneficial modifications can be termed plant growth regulation.

The compounds of the present invention are broadly active as plant growth modifiers. As such they are plant growth regulators and herbicides and frequently also serve as selective herbicides. The invention is particularly useful in the selective herbicide area to control particular weed species in the presence of specific crops (with little or no damage to the crops), for example to control such weeds as rhizomatous johnsongrass, annual grasses, yellow nutsedge and/or purple nutsedge in such crops as cotton, soybeans and corn.

DETAILED DESCRIPTION OF THE INVENTION

This invention relates to compounds of the formula

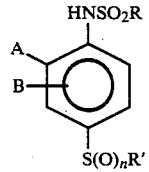

I wherein R is an alkyl group containing from 1 to 4 (preferably 1 to 2) carbon atoms or monohalomethyl (chloromethyl, bromomethyl, iodomethyl or fluoromethyl), R' is an alkyl group containing from 1 to 4 carbon atoms, A is halogen or $CF_3$, B is hydrogen or halogen and n is 0–2, provided that when A is $CF_3$, B is halogen, and agriculturally acceptable salts thereof.

The compounds of formula I wherein R is $-CH_2Cl$ and A is chlorine or bromine form a preferred class, and those compounds of formula I wherein R is $-CH_3$ and A is chlorine or bromine constitute a second preferred class, due in both cases to their highly useful activity.

It is an object of the invention to provide a method for modifying the growth of higher plants, including both plant growth regulating and herbicidal methods (the latter concerning killing or at least controlling the plants), said method comprising contacting the plants with an amount of compound of the invention effective to accomplish the desired result.

It is another object of the invention to provide a selective herbicidal method for killing or at least controlling the growth of a particular weed species in the presence of a specific crop, said method comprising contacting an area containing both types of plants with a concentration of a compound of the invention sufficient to kill or control the weed plants, but insufficient to have any substantial deleterious effect on the crop plants.

It is another object of the invention to provide compositions suitable for accomplishing the foregoing objects comprising a compound according to the present invention dispersed in an agriculturally acceptable extending medium.

The term agriculturally acceptable is utilized herein relative to the salts of the invention (in which the H in formula I is replaced by an agriculturally acceptable cation) and also relative to the extending media of the compositions of the invention. This term as utilized also includes "horticulturally acceptable" salts and media which are suitable for non-agricultural uses, for example the treatment of lawns and industrial turfs, etc.

The salts of the invention are generally metal, ammonium and organic amine salts and can be prepared by treating the acid-form compound with an appropriate base under mild conditions. Among the metal salts of the invention are alkali metal (e.g., lithium, sodium and potassium), alkaline earth metal (e.g., barium, calcium and magnesium) and heavy metal (e.g., zinc and iron) salts as well as other metal salts such as aluminum. Appropriate bases for use in preparing the metal salts include metal oxides, hydroxides, carbonates, bicarbonates and alkoxides. Some salts are also prepared by cation exchange reaction (by reacting a salt of the invention with an organic or inorganic salt in a cation exchange reaction). The organic amine salts include the salts of aliphatic (e.g., alkyl), aromatic and heterocyclic amines, as well as those having a mixture of these types of structures. The amines useful in preparing the salts of the invention can be primary, secondary or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the alkali metal, alkaline earth, ammonium and amine salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetones, etc. The resulting solution is then treated to remove the solvent, for example, by evaporation under reduced pressure.

The compounds of the invention can be prepared according to the following reaction sequence:

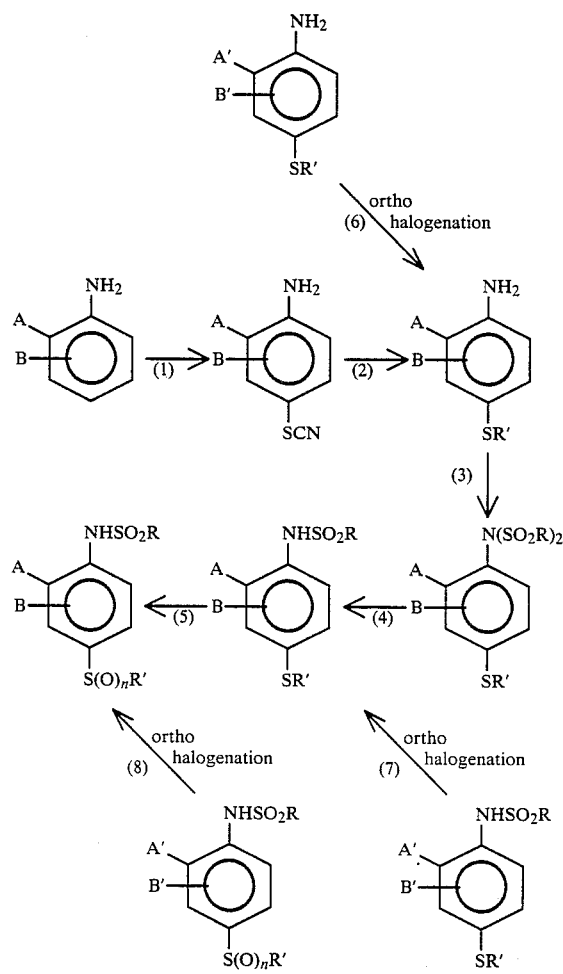

wherein A, B, R, R' and n are as in I and A' and B' are defined hereinafter.

The reaction of step (1) involves the formation of the substituted 4-thiocyanoanilines from the corresponding substituted anilines (which are known or for which the methods of preparation are well known) generally by conventional means.

The reaction of step (2) involves the formation of the substituted 4-alkylthioanilines directly from the corresponding 4-thiocyanoanilines. This reaction can be carried out utilizing various conventional techniques. For example, the thiocyano moiety can be alkylated in an alcoholic sodium cyanide solution. Preferably the alcohol has the same hydrocarbon residue as the desired alkyl group. Alternatively, a sodium mercaptide can be first formed from the thiocyano moiety and it can then be alkylated utilizing an alkylating agent such as an alkyl halide (methyl iodide).

Step (2) can also be carried out by first converting the sodium mercaptide to the free mercaptan by acidification. The mercaptan is then reacted with an alkylating agent such as an alkyl halide (methyl iodide) in the presence of an organic base. Suitable organic bases are tertiary amines such as triethylamine, dimethylcyclohexyl amine, pyridines and the like. This reaction is ordinarily preferred when the alkyl halide is a tert-butyl halide (tert-butyl bromide).

The reaction of step (3) is the alkanesulfonylation or halomethanesulfonylation of the product of step (2) with two or more equivalents of the sulfonyl chloride in the presence of a base. If one to two equivalents of the sulfonyl chloride are used, a mixture of mono- and bis-(sulfonylated) product can be obtained which may be used in step (4). If two or more equivalents of the chloride are reacted, the bis(sulfonylated) product is favored. Suitable bases for the reaction of step (3) are organic or inorganic bases such as pyridine, triethylamine, N,N-dimethylaniline and substituted pyridine, and the like. Liquid bases in excess can be used to eliminate the need for solvent. Stronger bases promote the formation of bis-(sulfonylated) product over the mono(sulfonylated) product.

Step (4) is the partial hydrolysis of the intermediate bis compounds. This is a high yield base hydrolysis reaction using a strong base such as potassium hydroxide in methanol. Alternatively, the precursor of step (3) can be converted directly to the product of step (4) by means of a mono(sulfonylation) reaction using one or more equivalents of base. This reaction is favored by a base weaker than pyridine, such as 3-bromopyridine.

Step (5) is carried out using conventional oxidation methods such as hydrogen peroxide in acetic acid, sodium metaperiodate and the like. The sulfoxide compound ($n=1$) is produced when equimolar amounts of the oxidizing agent and the reactant are utilized, whereas the sulfone ($n=2$) is prepared directly utilizing 2 moles (or a slight excess) of the oxidizing agent per mole of the reactant.

Steps (6), (7) and (8) are alternate routes to products of steps (2), (4) and (5), i.e., by halogenating unsubstituted ring position(s) ortho to the position carrying the amine or sulfonamide function. A' and B' represent the ring substituents resulting in A and B after the ortho halogenation. Suitable halogenating agents for steps (6), (7) and (8) are halogen and N-halosuccinimides (such as bromine, N-chlorosuccinimide and N-bromosuccinimide). It is presently preferred to prepare the compounds of the invention in which R' is tert-butyl by using either step (6), step (7) or step (8).

The herbicidal activity of the compounds of the invention has been determined using screening tests against greenhouse plantings. Both pre- and post-emergence activity are determined in a direct screen against selected weed species. The following weeds are examples of weeds which are used for these tests.

Grasses:
Giant foxtail (*Setaria faberi*)
Barnyardgrass (*Echinochloa crus-galli*)
Crabgrass (*Digitaria ischaemum*)
Quackgrass (*Agropyron repens*)
Yellow nutsedge (*Cyperus esculentus*)
Broadleaves:
Pigweed (*Amaranthus retroflexus*)
Purslane (*Portulaca oleracea*)

Wild mustard (*Brassica kaber*)
Field bindweed (*Convolvulus arvensis*)

The test chemicals are dissolved in a small amount of acetone or other suitable solvent and then diluted with water to give a concentration of 2000 ppm. From this concentration aliquots are diluted to give a final concentration of 500 ppm. Eighty ml. of this solution are added to a 6-inch pot containing the weed seeds to give a concentration equivalent to 20 lb/acre. Use of 20 ml. of said solution gives a concentration equal to 5 lb/acre. All subsequent waterings are made from the bottom. Two pots are used per treatment. Data are taken 2 to 3 weeks after treatment and recorded as percent pre-emergence kill for each species compared to the untreated controls.

To assess post-emergence activity, the same weed mixtures are allowed to grow from two to three weeks until the grasses are approximately 1 to 3 inches and the broadleaves 1 to 1½ inches tall. They are sprayed for approximately 10 seconds or until good wetting of the leaf surfaces occurs with a 2000 ppm solution as described above.

Data are taken two to three weeks after treatment and recorded as percent kill for each species compared to the untreated controls.

For application to plants, the compounds can be finely divided and suspended in any of the usual aqueous media. In addition, spreading agents, wetting agents, sticking agents or other adjuvants can be added as desired. Dry powders, as such or diluted with inert materials such as diatomaceous earth, can likewise be used as dusts for this purpose. The preparations are coated on the plants or the ground is covered when pre-emergence control is desired. Application rates are at 0.5 to 20 lbs/acre in general, but may be increased or reduced according to individual circumstances of use.

The compounds of the invention may be advantageously combined with other known herbicides to broaden or maximize the weed spectrum controlled by herbicidal compositions of this invention or to better control a weed not well controlled by specific compounds of the invention. Among these other known herbicides are phenoxy herbicides, e.g. 2,4-D, 2,4,5-T, silvex and the like, carbamate herbicides, thiocarbamate and dithiocarbamate herbicides, substituted urea herbicides, e.g. diuron, monuron and the like, triazine herbicides, e.g. simazine and atrazine, chloroacetamide and chlorinated aliphatic acid herbicides, chlorinated benzoic and phenylacetic acid herbicides such as chloramben and other herbicides such as trifluralin, paraquat, nitralin and the like. Furthermore, herbicidal compositions containing compounds of the invention may contain, in addition, nematicides, fungicides, insecticides, fertilizers, trace metals, soil conditioners, other plant growth regulators and the like. Such combinations are clearly envisioned in this invention.

The following examples are given for the purpose of further illustrating the present invention but are not intended, in any way, to be limiting on the scope thereof. All parts are given by weight unless otherwise specifically noted.

Referring to the reaction sequence set out previously, Examples 1 and 2 relate to the preparation of precursors of steps (1) and (6) and the remaining examples illustrate the steps of the process as follows:

| Example No. | Step No. |
| --- | --- |
| 3 | (1) |
| 4–6 | (2) |
| 7 | (3) |
| 8 | (4) |
| 9–10 | (3) and (4) |
| 11–12 | (5) |
| 13 | (6) |
| 14–15 | (7) |
| 16 | (8) |

EXAMPLE 1

5-Chloro-2-trifluoromethylaniline and 6-chloro-2-trifluoromethylaniline

A mixture of 3-chloro-2-nitrobenzoic acid (25 g., 0.12 mole) and sulfur tetrafluoride (42.1 g., 0.389 mole) is heated at 130° C. in a Hastelloy B reaction vessel for 16 hours. The unreacted sulfur tetrafluoride is vented through a scrubber, and the residual material is poured into a solution of sodium fluoride (6.2 g.) and water (200 ml.). Sodium carbonate is added to pH 8, and the basic mixture is extracted with ether. The combined ether extracts are washed with water and dried. Removal of the drying agent and ether gives 6-chloro-2-trifluoromethylnitrobenzene that is purified by chromatography on silica gel with a petroleum ether (b.p. 30°–60° C.)-ether eluant.

| Analysis: | % C | % H | % N |
| --- | --- | --- | --- |
| Calculated for $C_7H_3ClF_3NO_2$: | 37.37; | 1.34; | 6.21 |
| Found: | 36.8; | 1.2; | 5.9. |

The following compound is made using the same general method:

5-chloro-2-trifluoromethylnitrobenzene, a liquid.

Aqueous ammonium sulfide (60 g., 52–60%) is added dropwise to a warm (75° C.), stirred ethanol solution of 5-chloro-2-trifluoromethylnitrobenzene (22.6 g., 0.1 mole) and the resulting mixture is heated for four hours at a heating bath temperature of 97° C. and then allowed to cool to room temperature. The reaction mixture is poured into water, and the organic product is extracted with diethyl ether. After washing and drying the ether solution, the ether is removed by evaporation to give 5-chloro-2-trifluoromethylaniline.

The following compound is made in the same general way:

6-chloro-2-triflurormethylaniline.

EXAMPLE 2

4-Tert-butylthioaniline

To a stirred solution of lithium hydroxide monohydrate (21.0 g., 0.5 mole) and tert-butyl mercaptan (45.0 g., 0.5 mole) in dimethylformamide is added 4-chloronitrobenzene (78.75 g., 0.5 mole). After stirring the reaction mixture for 24 hours at room temperature, it is processed by pouring into water and the solid product collected by filtration. Recrystallization from methylene chloride-hexane gives pure 4-tert-butylthionitrobenzene, m.p. 40°–43° C.

| Analysis: | % C | % H | % N |
| --- | --- | --- | --- |
| Calculated for $C_{10}H_{13}NO_2S$: | 56.87; | 6.16; | 6.64 |

| Analysis: | % C | % H | % N |
| --- | --- | --- | --- |
| Found: | 56.6; | 6.4; | 6.7 |

4-Tert-butylthioaniline, m.p. 69°–72° C. is prepared from 4-tert-butylthionitrobenzene utilizing the general method of the second preparation of Example 1.

EXAMPLE 3

2-Bromo-4-thiocyananiline

To a cold (0°–5° C.), stirred solution of o-bromo-aniline (20.6 g., 0.12 mole) and sodium thiocyanate (29.2 g., 0.36 mole) in methanol (300 ml.) is added dropwise a solution of bromine (19.5 g., 0.122 mole) in methanol (75 ml.) saturated with sodium bromide. The solution is stirred for 1 hour following the addition of the bromine and then poured into water (2 liters) and neutralized with sodium carbonate. The resulting solid is collected, washed with water and dried, m.p. 74°–79° C.

The following compounds are prepared using the same general method:
2-chloro-4-thiocyanoaniline, m.p. 63°–65° C.
2-fluoro-4-thiocyanoaniline, m.p. 34°–35° C.
2,5-dichloro-4-thiocyanoaniline, m.p. 111°–115° C.
2,3-dichloro-4-thiocyanoaniline, m.p. 132°–137° C.
2-iodo-4-thiocyanoaniline, m.p. 92°–93° C.
5-chloro-4-thiocyano-2-trifluoromethylaniline, m.p. 75°–77° C.
2,5-dibromo-4-thiocyanoaniline, a solid
2,6-dichloro-4-thiocyanoaniline, m.p. 159°–161° C.
2,6-dibromo-4-thiocyanoaniline, m.p. 95°–102° C.
2,6-difluoro-4-thiocyanoaniline
2,5-difluoro-4-thiocyanoaniline.

EXAMPLE 4

2-Bromo-4-methylthioaniline

A solution of 2-bromo-4-thiocyanoaniline (11.5 g., 0.05 mole) and sodium cyanide (1.23 g., 0.025 mole) in methanol (100 ml.) is stirred at room temperature overnight. Sodium cyanide (0.025 mole) is then added and the reaction heated at reflux 2 hours and then cooled (0°–5° C.). Methyl iodide is added and stirring continued. Thin layer chromatography shows one product spot. Product is recovered by extraction with methylene chloride, 8.4 g.

The following additional compounds are prepared utilizing the same general method:
2-chloro-4-methylthioaniline, an oil.
2,3-dichloro-4-methylthioaniline, a solid.

EXAMPLE 5

2-Chloro-4-ethylthioaniline

A solution of 2-chloro-4-thiocyanoaniline (40 g., 0.22 mole) in ethanol (250 ml.) is added to a stirred solution of sodium sulfide nonahydrate (58.5 g., 0.22 mole) in water (110 ml.) and the mixture is warmed (50° C.) for 45 minutes. Ethyl iodide (36.6 g., 0.22 mole) is added and stirring is continued for 2 hours at 50° C. and then at room temperature overnight. The reaction is poured into water (3 liters) and the product extracted with either. The combined extracts are washed with water and dried (CaSO$_4$). Removal of the drying agent and solvent gives 2-chloro-4-ethylthioaniline, an oil.

The following additional compounds are prepared utilizing the same general method:
2-bromo-4-ethylthioaniline, an oil
2-fluoro-4-ethylthioaniline, an oil
2-chloro-4-isopropylthioaniline, an oil
2,5-dichloro-4-ethylthioaniline, an oil
2,3-dichloro-4-methylthioaniline, an oil
2-iodo-4-ethylthioaniline, an oil
2-fluoro-4-methylthioaniline, an oil
2-fluoro-4-isopropylthioaniline, an oil
2-iodo-4-methylthioaniline, an oil
2-iodo-4-isopropylthioaniline, an oil
2-bromo-4-isopropylthioaniline, an oil
2-chloro-4-isopropylthioaniline, an oil
2,3-dichloro-4-ethylthioaniline, an oil
2,5-dibromo-4-ethylthioaniline, an oil
2,5-dibromo-4-isopropylthioaniline, an oil
5-choro-4-ethylthio-2-trifluoromethylaniline, an oil.

EXAMPLE 6

2-Chloro-4-tert-butylthioaniline

A solution of 2-chloro-4-thiocyanoaniline (36.9 g., 0.20 mole) in ethanol (100–200 ml.) is added to a stirred solution of sodium sulfide nonahydrate (48.04 g., 0.20 mole) in water (100 ml.) and the mixture warmed (50° C.) for 90 minutes. The cool reaction mixture is poured into water (1 liter) and dilute hydrochloric acid added to bring the pH up to 6.0–6.5. The product is extracted with ether, the ether washed with water and then dried. Removal of the drying agent and ether leaves 2-chloro-4-mercaptoaniline as a yellow oil.

Dimethylcyclohexylamine (22.86 g., 0.18 mole) in methylene chloride (125 ml.) is added dropwise to a stirred solution of 2-chloro-4-mercaptoaniline (27.0 g., 0.17 mole) and tert-butyl bromide (22.86 g., 0.18 mole) in methylene chloride (125 ml.) and the mixture is allowed to stir at room temperature for about 68 hours. An additional quantity of dimethylcyclohexylamine (2.3 g.) and tert-butyl bromide (2.5 g., 0.018 mole) is added and stirring is continued overnight. The reaction is poured into water, and the product is extracted with methylene chloride. The combined extracts are washed with dilute hydrochloric acid, water and dried. Removal of the drying agent and methylene chloride gives impure 2-chloro-4-tert-butylthioaniline as a beige solid.

EXAMPLE 7

N-Chloromethylsulfonyl-2-chloro-4-ethylthio-chloromethanesulfonanilide

Chloromethanesulfonyl chloride (60 g., 0.4 mole) is added dropwise to a cold (0°–5° C.) stirred solution of 2-chloro-4-ethylthioaniline (15.1 g., 0.081 mole) in pyridine (104 ml.). The solution is stirred at room temperature and poured into ice water and 12N hydrochloric acid with stirring. The product is extracted into CH$_2$Cl$_2$, washed with water and dried. Removal of the drying agent and solvent gives crude product. Chromatography on silica gel with methylene chloride eluant gives pure product as an oil.

EXAMPLE 8

2-Chloro-4-ethylthiochloromethanesulfonanilide

A solution of N-chloromethylsulfonyl-2-chloro-4-ethylthiochloromethanesulfonanilide (7.2 g., 0.017 mole) and 85 percent potassium hydroxide (2.9 g.) in methanol is stirred about three days at room temperature. The solvent is removed by evaporation, the residue taken up in hot water, filtered, and the filtrate acidified with 12N hydrochloric acid. The product is recovered by filtration and air dried.

EXAMPLE 9

2-Bromo-4-methylthiochloromethanesulfonanilide

Chloromethanesulfonyl chloride (0.03 mole) is added dropwise to a cold (0.5° C.) stirred solution o-2-bromo-4-methylthioaniline (6.2 g., 0.028 mole) in pyridine (20 ml.). The solution is stirred at room temperature overnight, poured into ice water and 12N hydrochloric acid with stirring to give 2-bromo-4-methylthiochloromethanesulfonanilide as an oil. A methylene chloride solution of the oil is washed with water and dried. Removal of the drying agent and methylene chloride gives a red oil. Crystallization from methylene chloride-hexane gives a red-tan solid, m.p. 72°–85° C.

| Analysis: | % C | % H | % N |
|---|---|---|---|
| Calculated for $C_8H_9BrClNO_2S_2$: | 29.0; | 2.7; | 4.2 |
| Found: | 29.6; | 2.8; | 4.3. |

The following compounds are made using the same general method:
2-chloro-4-methylthiochloromethanesulfonanilide, m.p. 79°–82° C.
2-chloro-4-methylthiomethanesulfonanilide, m.p. 128°–133° C.
2,3-dichloro-4-methylthiochloromethanesulfonanilide, m.p. 119°–123° C.
2,3-dichloro-4-methylthiomethanesulfonanilide, m.p. 165°–170° C.
4-methylthiomethanesulfonanilide, m.p. 107.5°–110° C.

EXAMPLE 10

2-Chloro-4-ethylthiochloromethanesulfonanilide

Chloromethanesulfonyl chloride (4.0 g., 0.027 mole) is added dropwise to a stirred solution of 2-chloro-4-ethylthioaniline (5.0 g., 0.027 mole) in 3-bromopyridine (6.4 g., 0.041 mole), and the mixture is stirred overnight at room temperature. The reaction mixture is taken up in methylene chloride (200 ml.) and dilute hydrochloric acid (20%, 200 ml.), the layers are separated, and the methylene chloride solution is washed with dilute hydrochloric acid (10%, 200 ml.) three times and then dried (CaSO$_4$). Removal of the drying agent and solvent gives product as a reddish oil. This oil is taken up in hexane and cooled to give the product, 2-chloro-4-ethylthiochloromethanesulfonanilide, m.p. 70°–72° C.

| Analysis: | % C | % H | % N |
|---|---|---|---|
| Calculated for $C_9H_{11}Cl_2NO_2S_2$: | 36.0; | 3.7; | 4.7 |
| Found: | 36.3; | 3.5; | 4.7. |

Additional compounds prepared utilizing the same general method are as follows:
2-bromo-4-ethylthiochloromethanesulfonanilide, m.p. 63°–65° C.
2-chloro-4-isopropylthiochloromethanesulfonanilide, m.p. 50°–53° C.
2-fluoro-4-ethylthiochloromethanesulfonanilide, m.p. 78°–81° C.
2-chloro-4-ethylthiomethanesulfonanilide, m.p. 101°–103° C.
2-chloro-4-isopropylthiomethanesulfonanilide, m.p. 78°–80° C.
2-chloro-4-ethylthioethanesulfonanilide, m.p. 64°–66° C.
2-chloro-4-isopropylthioethanesulfonanilide, m.p. 52°–53° C.
2-bromo-4-ethylthiomethanesulfonanilide, m.p. 83°–85° C.
2-fluoro-4-ethylthiomethanesulfonanilide, m.p. 89°–91° C.
2,5-dichloro-4-ethylthiomethanesulfonanilide, m.p. 143°–144° C.
2-fluoro-4-ethylthioethanesulfonanilide, m.p. 77°–79° C.
2-fluoro-4-methylthioethanesulfonanilide, m.p. 69°–71° C.
2-fluoro-4-methylthiomethanesulfonanilide, m.p. 133°–135° C.
2-fluoro-4-methylthiochloromethanesulfonanilide, m.p. 88°–90° C.
2-bromo-4-isopropylthiomethanesulfonanilide, m.p. 82°–84° C.
2-bromo-4-isopropylthioethanesulfonanilide, m.p. 62°–64° C.
2-bromo-4-ethylthioethanesulfonanilide, m.p. 77.5°–79.5° C.
2-fluoro-4isopropylthiochloromethanesulfonanilide, an oil.
2-bromo-4-tert-butylthiochloromethanesulfonanilide, m.p. 100°–102° C.
2-iodo-4-ethylthiochloromethanesulfonanilide, m.p. 74°–76° C.
2,5-dichloro-4-ethylthiochloromethanesulfonanilide, m.p. 132.5°–134° C.
2,5-dibromo-4-ethylthiochloromethanesulfonanilide, m.p. 189°–195° C.
2,5-dibromo-4-isopropylthiochloromethanesulfonanilide, m.p. 132°–133° C.
2,3-dichloro-4-ethylthiochloromethanesulfonanilide, m.p. 92°–94° C.
2-bromo-4-isopropylthiochloromethanesulfonanilide, m.p. 56°–59° C.
2-chloro-4-tert-butylthiochloromethanesulfonanilide, m.p. 89°–90° C.
2-chloro-4-ethylthiofluoromethanesulfonanilide, m.p. 71°–72° C.
2-iodo-4-methylthiochloromethanesulfonanilide, m.p. 80°–82° C.
2-iodo-4-isopropylthiochloromethanesulfonanilide, an oil
4-tert-butylthiochloromethanesulfonanilide, m.p. 122°–124° C.
5-chloro-4-ethylthio-2-trifluoromethylmethansulfonanilide, m.p. 130°–131° C.
5-chloro-4-ethylthio-2-trifluoromethylethanesulfonanilide, m.p. 100°–102° C.
5-chloro-4-ethylthio-2-trifluoromethylchloromethanesulfonanilide, m.p. 128°–130° C.

EXAMPLE 11

2-Chloro-4-methanesulfinylchloromethanesulfonanilide

To a stirred solution of 2-chloro-4-methylthiochloromethanesulfonanilide (1.8 g., 0.0061 mole) in glacial acetic acid (20 ml.) is added 30 percent hydrogen peroxide (0.0061 mole). The solution is stirred overnight at room temperature, heated just to reflux, then treated with water. The aqueous mixture is extracted with methylene chloride, washed with water and dried. Removal of the drying agent and solvent gives a yellow oil. Crystallization from hexane produces a white solid; m.p. 99°–110° C.

| Analysis: | % C | % H | % N |
|---|---|---|---|
| Calculated for $C_8H_9Cl_2NO_3S_2$: | 31.8; | 3.0; | 4.6 |
| Found: | 31.8; | 3.0; | 4.7. |

The following compounds are prepared utilizing the same general method:

2-bromo-4-methanesulfinylchloromethanesulfonanilide, m.p. 108°–116° C.
2-bromo-4-ethanesulfinylchloromethanesulfonanilide, m.p. 157°–159° C.
2,3-dichloro-4-methanesulfinylchloromethanesulfonanilide, m.p. 153°–163° C.
2-chloro-4-methanesulfinylmethanesulfonanilide, m.p. 162°–165° C.
2-chloro-4-ethanesulfinylmethanesulfonanilide, m.p. 121°–123° C.
2-chloro-4-ethanesulfinylethanesulfonanilide, m.p. 109°–112° C.
2-bromo-4-ethanesulfinylmethanesulfonanilide, m.p. 119°–121° C.
2-fluoro-4-ethanesulfinylmethanesulfonanilide, m.p. 122°–124° C.
2-fluoro-4-ethanesulfinylethanesulfonanilide, m.p. 128°–130° C.
2-fluoro-4-methanesulfinylethanesulfonanilide, m.p. 111°–113° C.
2-bromo-4-isopropylsulfinylmethanesulfonanilide, m.p. 104°–106° C.
2-bromo-4-isopropylsulfinylethanesulfonanilide, m.p. 118°–120° C.
2-fluoro-4-methanesulfinylmethanesulfonanilide, m.p. 149°–150° C.
2-bromo-4-ethanesulfinylethanesulfonanilide, m.p. 113°–115° C.
2-fluoro-4-methanesulfinylchloromethanesulfonanilide, m.p. 118°–122° C.
2-fluoro-4-isopropylsulfinylchloromethanesulfonanilide, m.p. 118°–121° C.
2-bromo-4-tert-butylsulfinylchloromethanesulfonanilide, m.p. 112°–115° C.
2-iodo-4-ethanesulfinylchloromethanesulfonanilide, m.p. 165°–167° C.
2,5-dichloro-4-ethanesulfinylmethanesulfonanilide, m.p. 149°–150° C.
2,5-dichloro-4-ethanesulfinylchloromethanesulfonalide, m.p. 151°–154° C.
2,3-dichloro-4-ethanesulfinylchloromethanesulfonanilide, m.p. 118°–121° C.
2-chloro-4-ethanesulfinylchloromethanesulfonanilide, m.p. 146°–148° C.
2-chloro-4-isopropylsulfinylchloromethanesulfonanilide, m.p. 120°–122° C.
2-chloro-4-ethanesulfinylfluoromethanesulfonanilide, m.p. 130°–132° C.
2-iodo-4-methanesulfinylchloromethanesulfonanilide, m.p. 159°–161° C.

EXAMPLE 12

2-Chloro-4-methanesulfonylchloromethanesulfonanilide

To a stirred solution of 2-chloro-4-methylthiochloromethanesulfonanilide (3.0 g., 0.0101 mole) in glacial acetic acid (30 ml.) is added 30 percent hydrogen peroxide (0.0405 mole). The solution is heated at reflux for 2.5 hours, water is added, and the mixture is cooled. The resulting precipitate is collected by filtration, washed with water and dried to give a white solid, m.p. 172°–180° C.

| Analysis: | % C | % H | % N |
|---|---|---|---|
| Calculated for $C_8H_9Cl_2NO_4S_2$: | 30.2; | 2.8; | 4.4 |
| Found: | 30.2; | 2.8; | 4.4. |

Additional compounds prepared utilizing the same general method are as follows:

2-bromo-4-methanesulfonylchloromethanesulfonanilide, m.p. 156°–168° C.
2-bromo-4-ethanesulfonylchloromethanesulfonanilide, m.p. 120°–122° C.
2-chloro-4-ethanesulfonylchloromethanesulfonanilide, m.p. 146°–148° C. 2-chloro-4-isopropylsulfonylchloromethanesulfonanilide, m.p. 146°–149° C.
2-fluoro-4-ethanesulfonylchloromethanesulfonanilide, m.p. 143°–144° C.
2-chloro-4-methanesulfonylmethanesulfonanilide, m.p. 167°–169° C.
2-chloro-4-isopropylsulfonylmethanesulfonanilide, m.p. 142°–144° C.
2-chloro-4-ethanesulfonylethanesulfonanilide, m.p. 92°–94° C.
2-chloro-4-isopropylsulfonylethanesulfonanilide, m.p. 115°–117° C.
2-bromo-4-methanesulfonylmethanesulfonanilide, m.p. 170°–171.5° C.
2-bromo-4-ethanesulfonylmethanesulfonanilide, m.p. 122°–125° C.
2-fluoro-4-ethanesulfonylmethanesulfonanilide, m.p. 165°–167° C.
2,3-dichloro-4-methanesulfonylmethanesulfonanilide, m.p. 167°–180° C.
2-bromo-4-isopropylsulfonylmethanesulfonanilide, m.p. 133°–135° C.
2-bromo-4-isopropylsulfonylethanesulfonanilide, m.p. 110°–112° C.
2-fluoro-4-methanesulfonylchloromethanesulfonanilide, m.p. 153°–155° C.
2-fluoro-4-isopropylsulfonylchloromethanesulfonanilide, m.p. 140°–142° C.
2-bromo-4-tert-butylsulfonylchloromethanesulfonanilide, m.p. 169°–170° C.
2,5-dichloro-4-ethanesulfonylmethanesulfonanilide, m.p. 171°–174° C.
2,5-dichloro-4-ethanesulfonylchloromethanesulfonanilide, m.p. 182°–183° C.
2,3-dichloro-4-ethanesulfonylchloromethanesulfonanilide, m.p. 164°–166° C.
2-fluoro-4-methanesulfonylmethanesulfonanilide, m.p. 181°–183° C.
2-bromo-4-ethanesulfonylethanesulfonanilide, m.p. 88°–91° C.
2-iodo-4-ethanesulfonylchloromethanesulfonanilide, m.p. 130°–132° C.
5-chloro-4-ethanesulfonyl-2-trifluoromethylethanesulfonanilide, m.p. 144°–145° C.
3-chloro-4-ethanesulfonylfluoromethanesulfonanilide, m.p. 119°–120° C.
2-iodo-4-methanesulfonylchloromethanesulfonanilide, m.p. 194°–195° C.
2-iodo-4-isopropanesulfonylchloromethanesulfonanilide, m.p. 121°–123° C.

2,3-dichloro-4-methanesulfonylchloromethanesulfonanilide, m.p. 148°–151° C.

2,5-dibromo-4-ethanesulfonylchloromethanesulfonanilide, m.p. 144°–148° C.

EXAMPLE 13

4-Tert-butylthio-2-bromoaniline

To a cold (dry ice - acetone bath) stirred solution of 4-tert-butylthioaniline (25.6 g., 0.14 mole) in methylene chloride is added a slurry of N-bromosuccinimide (25.0 g., 0.14 mole) in methylene chloride in three equal portions. The reaction is allowed to come to room temperature with stirring overnight. The methylene chloride solution is washed with dilute aqueous sodium carbonate and water and then evaporated to give the desired product as a brown oil.

EXAMPLE 14

2-Bromo-4-methylthiomethanesulfonanilide

To a stirred mixture of 4-methylthiomethanesulfonanilide (7.6 g., 0.035 mole), iron filings (0.35 g.) and glacial acetic acid (50 ml.) is added bromine (5.6 g., 0.035 mole) dropwise. The reaction mixture is then heated at 110° C. for two hours, cooled and poured into water (300 ml.). The oil product is extracted with methylene chloride, the combined extracts washed with water and dried. Removal of the drying agent and solvent gives product as an oil. The oil is crystallized from hexane, and the tan solid recrystallized from hexane-methylene chloride to give a brown solid, m.p. 110°–110° C.

| Analysis: | % C | % H | % N |
|---|---|---|---|
| Calculated for $C_8H_{10}BrNo_2S_2$: | 32.4; | 3.4; | 4.7 |
| Found: | 33.1; | 3.4; | 4.7. |

EXAMPLE 15

4-Tert-butylthio-2-chlorochloromethanesulfonanilide

To a stirred solution of 4-tert-butylthiochloromethanesulfonanilide (1.47 g., 0.005 mole) in methylene chloride is added N-chlorosuccinimide (0.67 g., 0.005 mole). The reaction mixture is stirred at room temperature for about 72 hours and then processed in a conventional manner to give 2.1 g. of crude product. A pure sample is obtained by column chromatography over silica gel with methylene chloride eluant, m.p. 89°–91° C.

| Analysis: | % C | % H | % N |
|---|---|---|---|
| Calculated for $C_{11}H_{15}Cl_2NO_2S_2$: | 40.24; | 4.61; | 4.27 |
| Found: | 39.9; | 4.5; | 4.2. |

EXAMPLE 16

2-Bromo-4-methanesulfonyl-6-trifluoromethylmethanesulfonanilide

To a stirred mixture of 4-methanesulfonyl-2-trifluoromethylmethanesulfonanilide (2.6 g., 0.0082 mole), sodium acetate (0.74 g., 0.009 mole) and acetic acid (50 ml.) is added bromine dropwise (1.44 g., 0.009 mole). The reaction mixture is stirred at room temperature for about 24 hours then heated at 110° C. for about 24 hours. The cooled reaction mixture is poured into water and the solid product is collected by filtration. A pure sample is obtained by recrystallization from methylene chloride-acetone. M.p. 214°–220° C.

| Analysis: | % C | % H | % N |
|---|---|---|---|
| Calculated for $C_9H_9BrF_3NO_4S_2$: | 27.3; | 2.3; | 3.5 |
| Found: | 27.5; | 2.4; | 3.5. |

What is claimed is:

1. A compound of the formula

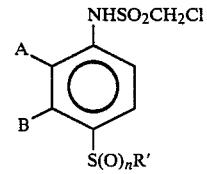

wherein R' is an alkyl group containing from 1 to 2 carbon atoms, A is chlorine or bromine, B is hydrogen or chlorine or an n is 0–2 and agriculturally acceptable salts thereof.

2. 2-Chloro-4-methanesulfonylchloromethanesulfonanilide or an agriculturally acceptable salt thereof.

3. 2-Bromo-4-ethanesulfonylchloromethanesulfonanilide or an agriculturally acceptable salt thereof.

4. A method of controlling undesired plants which comprises applying to said plants a herbicidially effective amount of a compound of claim 1.

* * * * *